(12) United States Patent
Basile et al.

(10) Patent No.: US 11,123,499 B2
(45) Date of Patent: Sep. 21, 2021

(54) PREFILLED DISPOSABLE INJECTION DEVICE

(71) Applicant: Merck Sharp & Dohme Corp., Rahway, NJ (US)

(72) Inventors: Peter A. Basile, Bloomsbury, NJ (US); Steven Carl Persak, Basking Ridge, NJ (US); Mikhail Gotliboym, Scotch Plains, NJ (US); Brad Britland, Lake Hopatcong, NJ (US); Stephen G. Miggels, Wyckoff, NJ (US); Henry J. Mack, Jr., Phillipsburg, NJ (US); Oliver J. Sha, Randolph, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 231 days.

(21) Appl. No.: 16/069,331

(22) PCT Filed: Jan. 13, 2017

(86) PCT No.: PCT/US2017/013278
§ 371 (c)(1),
(2) Date: Jul. 11, 2018

(87) PCT Pub. No.: WO2017/127287
PCT Pub. Date: Jul. 27, 2017

(65) Prior Publication Data
US 2019/0022336 A1    Jan. 24, 2019

Related U.S. Application Data

(60) Provisional application No. 62/280,214, filed on Jan. 19, 2016.

(51) Int. Cl.
*A61M 5/50* (2006.01)
*A61M 5/31* (2006.01)
(Continued)

(52) U.S. Cl.
CPC ............... *A61M 5/50* (2013.01); *A61M 5/00* (2013.01); *A61M 5/178* (2013.01); *A61M 5/24* (2013.01);
(Continued)

(58) Field of Classification Search
CPC .............. A61M 5/1454; A61M 5/2422; A61M 5/2425; A61M 5/281; A61M 5/282;
(Continued)

(56) References Cited

U.S. PATENT DOCUMENTS 2,950,717 A * 8/1960 Bouet .................... A61J 1/062
604/214
3,340,869 A    9/1967 Bane
(Continued)

FOREIGN PATENT DOCUMENTS

WO    WO2015187518 A1    12/2015
WO    WO2017127287 A1    7/2017

*Primary Examiner* — James D Ponton
(74) *Attorney, Agent, or Firm* — Janet E. Fair; Alysia A. Finnegan

(57) ABSTRACT

The present invention relates to drug delivery systems that cannot be reloaded or reused and further include a passive safety shield system. The drug delivery devices described herein include a drug container comprising at least one bellow, a needle, wherein the needle is in liquid communication with the drug container; a plunger extending between a proximal end and a distal end, wherein the plunger is in communication with the drug container and where upon axial movement of the plunger, the drug container is compressed.

4 Claims, 15 Drawing Sheets

(51) Int. Cl.
*A61M 5/00* (2006.01)
*A61M 5/315* (2006.01)
*A61M 5/32* (2006.01)
*A61M 5/178* (2006.01)
*A61M 5/24* (2006.01)

(52) U.S. Cl.
CPC ............ *A61M 5/2425* (2013.01); *A61M 5/31* (2013.01); *A61M 5/315* (2013.01); *A61M 5/3129* (2013.01); *A61M 5/3146* (2013.01); *A61M 5/31511* (2013.01); *A61M 5/32* (2013.01); *A61M 5/326* (2013.01); *A61M 5/3271* (2013.01); *A61M 2005/2407* (2013.01); *A61M 2005/2433* (2013.01); *A61M 2205/273* (2013.01); *A61M 2207/00* (2013.01)

(58) Field of Classification Search
CPC ...... A61M 5/50; A61M 5/5013; A61M 5/502; A61M 5/3243; A61M 2005/3261; A61M 2005/3264; A61M 2005/3263; A61M 2205/273; A61M 2205/276; A61M 5/3146; A61M 5/31511; F16F 1/32; F16F 1/322
See application file for complete search history.

(56) References Cited

U.S. PATENT DOCUMENTS

| | | | |
|---|---|---|---|
| 3,473,524 A | 10/1969 | John | |
| 3,938,514 A | 2/1976 | Boucher | |
| 4,822,332 A * | 4/1989 | Kajander | A61F 13/263 604/16 |
| 5,135,498 A * | 8/1992 | Kam | A61M 5/1483 128/DIG. 12 |
| 5,163,918 A * | 11/1992 | Righi | A61M 5/326 604/198 |
| 5,295,975 A | 3/1994 | Lockwood, Jr. | |
| 5,407,431 A | 4/1995 | Botich et al. | |
| 5,693,021 A | 12/1997 | Diaz et al. | |
| 5,873,860 A * | 2/1999 | Kahlert | A61M 5/002 604/212 |
| 6,319,235 B1 | 11/2001 | Yoshino | |
| 6,916,305 B2 | 7/2005 | Jones et al. | |
| 7,824,379 B2 * | 11/2010 | Doyle | A61M 5/3137 604/198 |
| 8,608,693 B2 | 12/2013 | Westbye | |
| 8,858,510 B2 | 10/2014 | Karlsson | |
| 2002/0091361 A1 * | 7/2002 | Rosoff | A61M 5/282 604/212 |
| 2005/0171477 A1 * | 8/2005 | Rubin | A61M 5/2033 604/156 |
| 2007/0191780 A1 * | 8/2007 | Modi | A61M 5/282 604/187 |
| 2008/0243077 A1 * | 10/2008 | Bivin | A61M 35/003 604/131 |
| 2011/0218499 A1 | 9/2011 | Cahen | |
| 2012/0101475 A1 | 4/2012 | Wilmont et al. | |
| 2012/0220948 A1 | 8/2012 | Barbour | |
| 2013/0281940 A1 | 10/2013 | Gelblum et al. | |
| 2015/0141934 A1 * | 5/2015 | Gardner | A61M 5/2425 604/216 |

* cited by examiner

PREFILLED DISPOSABLE INJECTION DEVICE

CROSS-REFERENCE TO RELATED APPLICATIONS

This application is a U.S. National Phase application under 35 U.S.C. § 371 of PCT Application No. PCT/US2017/013278, filed Jan. 13, 2017, which published as WO2017/127287 A1 on Jul. 27, 2017, and claims priority under 35 U.S.C. § 365(b) from U.S. provisional patent application No. 62/280,214, filed Jan. 19, 2016.

FIELD OF THE INVENTION

The present invention relates generally to drug delivery devices. Specifically, the invention is directed to drug delivery devices that incorporate a passive shield system for protection against accidental needle stick injury. The drug delivery devices of the present invention cannot be refilled post use, preventing possible re-use of the drug delivery device.

BACKGROUND

In many cases, it is not only the cost of a drug that prohibits a treatment from becoming widely accessible but also the cost of packaging. Many companies strive to reduce the cost of proven life-saving treatments so that such treatments can be more readily accessible.

Reducing the cost of traditional packaging is one example of a way to lower the cost of such treatments. Reducing the cost of traditional packaging of pre-filled syringes has been an area of focus for some time. The problem with traditional packaging of pre-filled syringes is two-fold. The first is the cost of the primary glass drug container. The second is the cost of filling the glass container. Manufacturing and filling, are by their very nature, two distinct processes. The first step is to form the container and then one must pack it up and ship it. Then the container must be unpacked at the container filling facility and then filled.

An additional problem that plagues conventional syringes is that conventional syringes can be refilled and reused. Re-using syringes contributes to the transmission of blood borne diseases like HIV. Moreover, even if re-using the syringe is not the intention, inherent in all syringes, whether pre-filled or not, is the risk of accidental needle stick. Therefore, not only is there a need for low-cost syringes that cannot be refilled or reused, there is a need for such syringes that further incorporate a passive shield system for shielding the needle, thus providing further safety to the user.

SUMMARY

The drug delivery device described herein provides a solution to the problems of traditional syringes discussed above.

For the purpose of clarity, orientation references are hereby established for the description of this invention. The term "proximal" refers to a position that is close to the body of the person injecting a drug into the patient with the device. The term "distal" refers to a position that is away from the body of the person injecting the drug into the patient with the device.

Described herein are drug delivery systems that cannot be reloaded or reused, such as those described in WO2015/134307 and PCT/US15/033450, and further include a passive safety shield system. As used herein, a "passive shield system" or "passive safety shield system" is a system that deploys a needle shield (or safety shield) automatically, requiring no additional actions by the user other than what is required to administer the contents of the drug delivery device into a patient.

Described herein are drug delivery devices that cannot be refilled or reused post use and incorporate a passive shield system. In accordance with the embodiments described herein, the user is able to cause the shielding of a needle of a drug delivery device by simply applying pressure to the plunger of the drug delivery device following injection of the contents of the drug container and removal of the needle from the patient. The shield may accordingly be deployed automatically through the use of only one hand. As there is no need to place the hand near the needle for any purpose, the risk of needle stick injury is reduced.

The drug delivery devices described herein comprise a main body which houses a plunger, a drug container and a spring; and a needle in fluid connection with the drug container.

The main body of the presently described drug delivery device includes at least an inner body coupled to an outer body, wherein the inner body defines an enclosure. The enclosure houses the drug container and the plunger, wherein the plunger is slidable within the enclosure. It is the outer body which provides the shield that, after injection and removal of the needle from the patient, shields the needle from the user. To do so, the outer body is axially movable with respect to the inner body between retracted and extended positions. The outer body is intended to cover the needle tip when in the extended position.

The spring is located between the outer body and the inner body. The spring is preferably orientated with respect to the main body such that an end of the spring engages a part of the outer body, and the opposite end of the spring engages a part of the inner body. The purpose of the spring is to urge the outer body towards the extended position at the appropriate time during injection.

The main body of the present drug delivery device which incorporates a passive safety shield system facilitates the safe use of prefilled syringes, though it can be adapted for other sharp-pointed medical devices, such as syringes filled just before use, as well. When employed with a syringe, the system allows the contents of the syringe to be expressed in a conventional manner.

In certain embodiments of the drug delivery device described herein, complementary structure is provided on the outer body and inner body to releasably retain the outer body in the retracted position. Complementary structure is also provided on the outer body and inner body to lockingly retain the outer body in the extended position.

For example in certain embodiments, the outer body comprises a pair of release and lock beams and the inner body comprises a set of first locking windows and a set of second locking windows. When the set of release and lock beams are in communication with the first set of locking windows on the inner body, the outer body is in a first or retracted positon. The force of the spring, by itself, is insufficient to cause disengagement of the release and lock beams from the first set of complementary locking windows on the inner body. However, in this embodiment, the plunger is operationally coupled to the inner body such that sufficient axial movement of the plunger causes disengagement of the release and lock beams of the outer body from the complementary first set of locking windows on the inner body. Such movement of the plunger is ordinarily caused by pressure on the plunger of the drug delivery system following the injection of the contents of the drug container and after removal of the needle from the patient. Upon disengagement of the release and lock beams of the outer body from the complementary first set of locking windows on the inner body, the spring causes the outer body to move to the extended position.

In certain embodiments, disengagement is caused by release cams located on the plunger, such that as pressure is applied to the proximal end of the plunger and it moves axially toward the needle, the release cams displace the release and lock beams of the outer body from the first set of complementary locking windows on the inner body. The axial movement of the outer body is preferably limited by a second set of complementary locking windows on the inner body. Thus, as the outer body moves slidingly over the inner body, the release and lock beams will engage the second set of locking windows, locking the outer body in a second or extended position.

In other embodiments of the of the drug delivery device described herein, the main body has an inner body and an outer body, wherein the outer body further comprises a cam track. In such an embodiment, the plunger further comprises a cam follower which is capable of following the cam track. When the outer body is in the retracted position, the force of the spring, by itself, is insufficient to cause the cam follower to begin to go down the cam track. However, the plunger is operationally coupled to the main body such that sufficient axial movement of the plunger causes the cam follower to travel down the cam track. As the plunger moves axially within the main body, the outer body and plunger rotate with respect to one another as driven by the cam follower. At the end of the injection, the cam follower has reached a point within the cam track wherein the force of the spring is now, by itself, sufficient to cause the outer body to slidely move over the inner body and to move to the extended position.

The axial movement of the outer body is preferably limited by a portion of the cam track that prevents the cam follower from moving any further.

In certain embodiments, the plunger not only includes a cam follower but also a freely-rotating top at the proximal end of the plunger. Such a top allows the plunger and outer body of the main body to rotate freely so as to allow the cam follower to follow the cam track. Alternatively, the plunger can include a freely-rotating bolt at the distal end of the plunger. In certain embodiments, the cam follower is located on the freely-rotating bolt. This again allows the plunger and outer body of the main body to rotate freely so as to allow the cam follower to follow the cam track.

In other embodiments of the drug delivery device described herein, the main body further comprises an intermediate tube located between the inner body and the outer body, and wherein the inner body extends between a proximal end and a distal end and the outer body extends between a proximal end and a distal end and wherein the distal end of the outer body and distal end of the inner body are releasably engaged and wherein as the intermediate tube moves axially between the inner body and outer body, the intermediate tube causes the inner body and outer body to disengage. As the plunger moves axially within the inner body, pressure is applied to the intermediate tube, causing it to move axially as well. The intermediate tube causes disengagement between the distal end of the inner body and the distal end of the outer body. Upon disengagement of the inner body from the outer body, the spring urges the outer body to axially move to the extended position.

In other embodiments, the outer body comprises two pairs of release and lock tabs and the inner body comprises a set of viewing windows to view the drug container. When the first set of release and lock tabs are in communication with the viewing windows on the inner body, the outer body is in a first or retracted positon. The force of the spring, by itself, is insufficient to cause disengagement of the release and lock tabs from the viewing windows on the inner body. However, in this embodiment, the plunger is operationally coupled to a screw housed by the inner body such that sufficient axial movement of the plunger causes axial movement of the screw and the raised helical threads on the screw causes disengagement of the first pair of release and lock tabs of the outer body from the viewing windows on the inner body. Such movement of the plunger is ordinarily caused by pressure on the plunger of the drug delivery system following injection of the contents of the drug container and removal of the needle from the patient. Upon disengagement of the first set of release and lock tabs of the outer body from the viewing windows on the inner body, the spring causes the outer body to move to the extended position. The axial movement of the outer body is stopped by the second set of release and lock tabs on the outer body connecting and attaching to the viewing window of the inner body.

In certain embodiments of the drug delivery devices described herein, the drug delivery devices comprise a drug container comprising at least one bellow, wherein in the at least one bellow comprises a first surface and an opposing second surface, wherein the first surface is comprised of a first Belleville spring and the opposing second surface is comprised of a second Belleville spring, wherein the second Belleville spring has a higher spring rate than the first Belleville spring.

As used herein, "bellow" means a flexible structure whose volume can be changed by compression or expansion.

With regard to the bellows contained in the drug delivery device described herein, when an axial tensile force is applied to a bellow, the Belleville springs are pulled apart. In this position, the bellow is expanded and the volume contained within the bellow is maximized.

When an axial compressive force is applied to the bellow, the Belleville springs are forced together such that their opposing internal surfaces abut each other. The first Belleville spring is softer and is proportioned such that when it is compressed, it passes through the neutral position into a second stable position where it abuts the second Belleville spring. The second stable position is a mirror image of the first, expanded position. Due to the relative spring rates and selected geometries, when an axial compressive load is applied to this set of Belleville springs, the second, stiffer, spring remains relatively static and the first, softer, spring deflects. When it is fully deflected into the second position, the bellow is compressed and volume contained within the bellow is minimized.

As used herein, "belleville spring" means a type of spring shaped like a washer that is three dimensional, wherein the inner diameter resides in a plane which is above the outer diameter's plane i.e. a frusto-conical shape, which gives the washer a spring characteristic. Belleville spring, disc spring, Belleville washer, conical compression washer, are all names for the same type of spring.

As used herein, "spring rate", is the relationship between the degree of deflection of a spring and the spring force generated in response to this deflection.

In certain embodiments, the drug delivery devices described herein contain a drug container that is comprised of at least one bellow with unique geometry comprising two opposing Belleville springs. This unique geometry prevents the drug container from restoring itself to its original or post-injection state once the drug product loaded into the container has been dispensed. This precludes the possibility of the drug delivery device from being refilled or re-used. This unique geometry also allows the drug container to have minimum residual volume when collapsed post-use, allowing the drug loaded into the drug container to be dispensed leaving no residual, wasted drug product in the container.

The drug delivery device described herein includes a drug container comprising at least one bellow that has a first surface and a second surface. The surfaces are formed by two opposing Belleville springs, a first Belleville spring forming the first surface and a second Belleville spring forming the second surface. The second Belleville spring is stiffer and has a higher spring rate then the first Belleville spring. The first Belleville spring is softer and is proportioned such that when it is compressed into the flat state, it snaps through the flat position into a second stable position. This second stable position is a mirror image of the initial, unstressed position. Due to the relative spring rates and selected geometries, when an axial load is applied to this set of Belleville springs, the second and stiffer spring remains relatively static; the first, softer spring begins to deflect. When it is deflected into its flat position it snaps through this position and becomes inverted.

This behavior produces two distinct benefits. First, as the first Belleville spring is now inverted and is nesting inside of the stiffer second Belleville spring, the residual volume of the bellow is a small fraction of the initial volume of the bellow when the bellow was in its original or starting position. Second, since the inverted state of the first Belleville spring is also stable, there is no restoring force. Because of this, there is no concern for "suck back" of the delivered drug product. Additionally, since there is no restoring force, the device cannot be refilled and reused.

By way of contrast, with conventional bellows the convolutions are mirror images, identical on either side of the fold or corrugation. Although conventional bellows can compress when an axial load is applied, the residual volume is substantial, and the bellows will recover to its initial geometry when the axial load is released. If conventional bellows were to be used in conjunction with a drug container for a drug delivery device, the substantial residual volume could contribute to a costly amount of unused drug product left in the device. Additionally, as conventional bellows return to its uncompressed state there is a risk of creating a vacuum which can lead to "suck-back" of drug product and under dosing. Also, because conventional bellows can easily return to their uncompressed state and create a vacuum, there is a possibility that the drug delivery device can be refilled and reused which can contribute to the spread of infectious diseases.

Alternatively, in certain embodiments of the drug delivery devices described herein, the drug delivery devices comprise a drug container comprising a continuous change in cross section from its proximal end to distal end. In such embodiments, the cross-section of the drug container changes from its distal end to its proximal end. In certain embodiments, the drug container tapers from its distal end to its proximal end. This geometry allows the proximal end of the tube to fold on itself and constrict as the drug delivery device is being used. In certain embodiments, as the drug delivery device is being used, the proximal end of the drug container is twisted and the distal end remains stationary. Twisting initiates at the proximal end since this is the weakest cross section of the drug container. As the twisting motion continues, the constriction moves distally, emptying the contents of the drug container, delivering the drug to the patient.

Also described herein are methods of manufacturing the drug containers and the drug delivery devices described herein. In certain embodiments, the drug container is made using blow-fill-seal technology. In another embodiment, the drug container is made using form-fill-seal technology.

As an example, the drug delivery devices described herein includes, a drug delivery device comprising a drug container comprising at least one bellow, wherein in the at least one bellow comprises a first surface and an opposing second surface, wherein the first surface is comprised of a first Belleville spring and the opposing second surface is comprised of a second Belleville spring, wherein the second Belleville spring has a higher spring rate than the first Belleville spring; or a drug container extending between distal and proximal ends, and comprises a continuous change in cross section from proximal end to distal end; a needle, wherein the needle is in liquid communication with the drug container; a plunger wherein the plunger extending between a proximal end and a distal end and wherein the plunger is in communication with the drug container where upon axial movement of the plunger, the drug container is compressed; a main body extending between a proximal end and a distal end and comprising an inner body and an outer body, wherein the inner body houses the plunger and the drug container and the outer body is capable of sliding over the inner body and extending past the needle; and a spring located between the inner body and the outer body for urging the outer body to slide over the inner body and extend past the needle.

In certain embodiments of the drug delivery devices described herein, the outer body further comprises a set of release and lock beams, and wherein the inner body further comprises a first set of locking windows, wherein when the first set of locking beams is engaged with the first set of locking windows the outer body is in a retracted position.

In certain embodiments of the drug delivery devices described herein, the plunger comprises at least one release cam where upon axial movement of the plunger, the release cam can cause disengagement of the set of release and lock beams of the outer body from the first set of locking windows from the inner body causing the outer body to move slidingly along the inner body.

In certain embodiments of the drug delivery devices described herein, the inner body further comprises a second set of locking windows, wherein when the set of release and lock beams is engaged with the second set of locking windows the outer body is in an extended position.

In certain embodiments of the drug delivery devices described herein, the outer body further comprises a cam track and wherein the plunger further comprises a cam follower wherein the cam follower is capable of traveling along the cam track.

In certain embodiments of the drug delivery devices described herein, the plunger further comprises a freely-rotating top at the proximal end of the plunger, wherein the freely rotating top allows the plunger to rotate with respect to the outer body to allow the cam follower to travel along the cam track.

In certain embodiments of the drug delivery devices described herein, the outer body comprises a cam track and wherein the plunger comprises a freely-rotating bolt at the distal end of the plunger, wherein the freely-rotating bolt comprises a cam follower wherein the freely rotating bolt allows the cam follower to travel along the cam track.

In certain embodiments of the drug delivery devices described herein, the main body further comprises an intermediate tube located between the inner body and outer body, and wherein the inner body extends between a proximal end and a distal end and the outer body extends between a proximal end and a distal end and wherein the distal end of the outer body and distal end of the inner body are releasably engaged and wherein as the intermediate tube moves axially between the inner body and outer body, the intermediate tube causes the inner body and outer body to disengage.

In certain embodiments, the drug delivery devices described herein, further comprise a screw housed in the inner body and in communication with the plunger, and wherein the inner body comprises a pair of viewing windows and the outer body comprises two pairs of release and locking tabs, a first set of release and lock tabs and a second set of release and lock tabs.

In certain embodiments of the drug delivery devices described herein, the drug container comprises at least one bellow, wherein in the at least one bellow comprises a first surface and an opposing second surface, wherein the first surface is comprised of a first Belleville spring and the opposing second surface is comprised of a second Belleville spring, wherein the second Belleville spring has a higher spring rate than the first Belleville spring.

In certain embodiments of the drug delivery devices described herein, the drug container extends between distal and proximal ends, and comprises a continuous change in cross section from proximal end to distal end.

In certain embodiments the drug delivery devices described herein, are manufactured using blow-fill-seal technology.

In certain embodiments the drug delivery devices described herein, are manufactured using form-fill-seal technology.

In certain embodiments the drug delivery devices described herein, the drug container further comprises a product.

Suitable drug products include, but are not limited to, one or more of the following: human papillomavirus quadrivalent vaccine, recombinant; human papillomavirus 9-valent vaccine, recombinant; *Haemophilus* B conjugate vaccine or meningococcal protein conjugate; hepatitis B vaccine, recombinant; *Haemophilus* B conjugate; hepatitis B (recombinant) vaccine; hepatitis A vaccine, inactivated; pneumococcal vaccine polyvalent; artemether; cyclimorph (morphine and cyclizine); cyclizine; morphine; codeine; chlorphenamine; fosphenytoin sodium; chlorpromazine; haloperidol; epinephrine; hydroxocobalamin; heparin sodium; phytomenadione; atropine; furosemide; lidocaine; dalteparin sodium; digoxin; amiodarone; dextran 70; glucagon-like peptide; polygeline; hyoscine hydrobromide; oxytocin and ergometrine; oxytocin; carbetocin; magnesium sulfate; dexamethasone; metooclopramide; ondansetron; ketamine; neostigmine; pyridostigmine; dimercaprol; ranitidine; testosterone; calcium gluconate; diazepam; acetylcysteine; sulfamethoxazole+trimethoprim; hydroxocobalamin; protamine sulfate; tranexamic acid; verapamil; anti-D immunoglobulin (human); diphtheria antitoxin; suxamethonium; fluphenazine; salbutamol; pediatric hexavalent combination vaccine for *Haemophilus* influenzae type B conjugate, recombinant hepatitis B surface antigen, diphtheria, tetanus, 5-component acellular pertussis, and inactivated poliovirus Types 1, 2, and 3; BCG Vaccine; cholera vaccine; dengue vaccine; diphtheria vaccine; ebola vaccine; *Haemophilus* influenzae type B vaccine; herpes simplex virus vaccine; influenza vaccine; Japanese encephalitis vaccine; measles vaccine; meningococcal meningitis vaccine; mumps vaccine; norovirus vaccine; pertussis vaccine; pneumococcal vaccine; poliomyelitis vaccine; rabies vaccine; respiratory syncytial virus vaccine; rotavirus vaccine; rubella vaccine; tetanus vaccine; typhoid vaccine; varicella vaccine; yellow fever vaccine.

BRIEF DESCRIPTION OF THE FIGURES

The foregoing and other features and advantages of the invention will be apparent from the following, more particular description of a preferred embodiment of the invention, as illustrated in the accompanying drawings wherein like reference numbers generally indicate identical, functionally similar, and/or structurally similar elements.

DESCRIPTION

Figure 1:
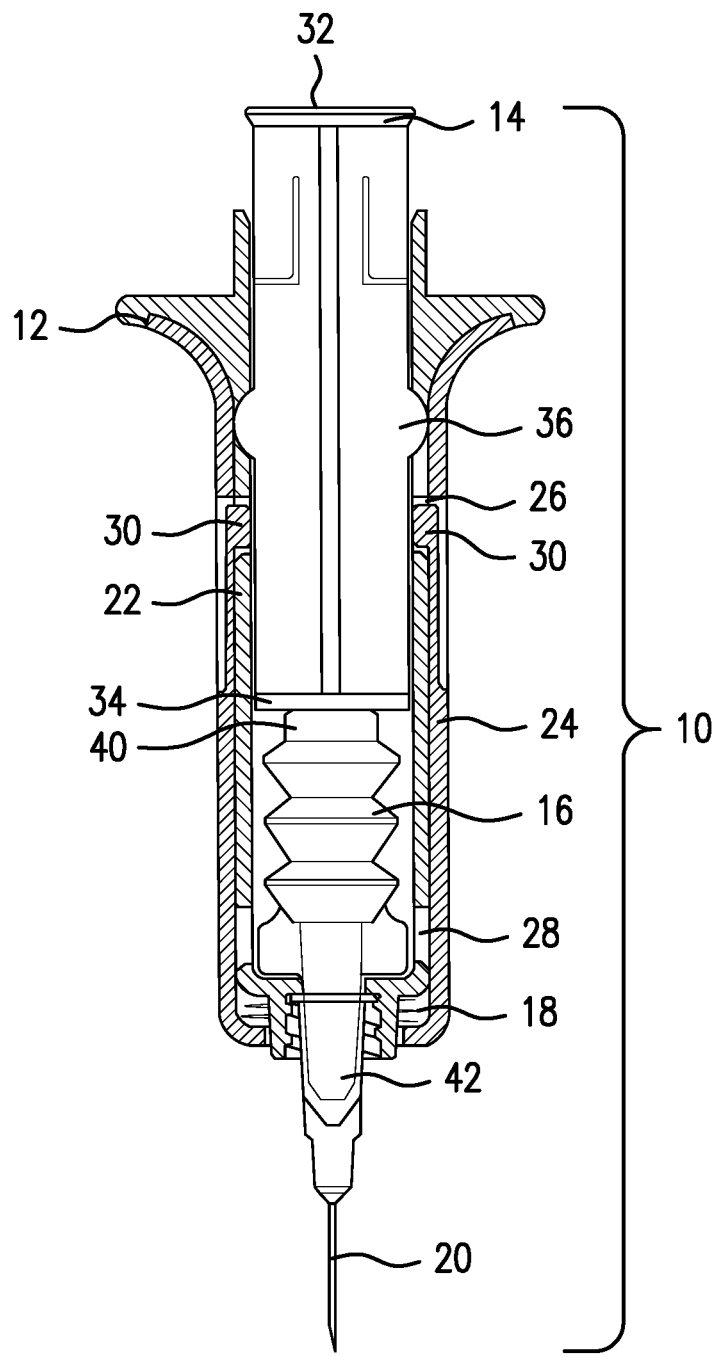
FIG. 1 is an embodiment of the drug delivery device described herein, in its pre-injection position or first position wherein the safety shield is in a retracted state.

Referring to the figures, wherein like reference numbers designate like elements throughout the drawings, FIG. 1 shows an embodiment of the drug delivery device described herein, in its pre-injection position or first position wherein the safety shield is in a retracted state. FIG. 1 shows a drug delivery device 10 that comprises a main body 12, a plunger 14, a drug container 16, a spring 18 and a needle 20. The main body 12 includes an inner body 22 and an outer body 24. As shown in FIG. 1, the inner body 22 has a first set of locking windows 26 and a second set of locking windows 28. The outer body 24 contains two release and lock beams 30. The outer body 24 is attached to the inner body 22 by the release and lock beams being in communication with the first set of locking windows 26 or second set of locking windows 28. Specifically, as shown in FIG. 1, the outer body 24 is secured in the retracted position as the release and lock beams 30 are in communication with the first set of locking windows 26.

Also, as shown in FIG. 1, the plunger 14 extends from a proximal end 32 to a distal end 34 and has release cams 36. As pressure is applied to the plunger 14 at the proximal end 32, the plunger 14 moves axially toward the drug container 16, causing the drug container 16 to compress. As the release cams 36 on the plunger 14 arrive at the first set of locking windows 26, the release cams 36 displace the release and lock beams 30 causing them to disengage from the first set of locking windows 26.

Once the release and lock beams 30 disengage from the first set of locking windows 26, the spring 18 urges the outer body 24 to extend axially to shield the needle 20. This extended position is shown in FIG. 2.

FIG. 1 also shows a drug container 16 comprising bellows, the bellows are formed by two opposing Belleville springs, a first Belleville spring forming the first surface and a second Belleville spring forming the second surface. The second Belleville spring is stiffer and has a higher spring rate then the first Belleville spring. The first Belleville spring is softer and is proportioned such that when it is compressed into the flat state, it snaps through the flat position into a second stable position. This second stable position is a mirror image of the initial, unstressed position. Due to the relative spring rates and selected geometries, when an axial load is applied to this set of Belleville springs, the second and stiffer spring remains relatively static; the first, softer spring begins to deflect. When it is deflected into its flat position it snaps through this position and becomes inverted.

As shown in FIG. 1, the drug container 16 has a top 40 located at the proximal end of drug container 16 and an outlet port 42 located at the distal end of drug container 16. Top 40 is axially aligned with the bellows and outlet port 42 is axially aligned with the bellows. In the embodiment shown in FIG. 1, the top 40 of drug container 16 is a priming bellow which requires less force to compress than the remaining bellows of drug container 16, whereby application of compressive force to the drug container 16 causes the priming bellow to compress first. In this embodiment, the priming bellow can function to evacuate trapped air or other fluid from the drug container 16 prior to dispensing of the drug. In certain embodiments, the priming bellow comprises a first Belleville spring and a second Belleville spring. The first Belleville spring of the priming bellow has a lower spring rate than the remaining Belleville springs in the drug container. In certain embodiments, the outer diameter of priming bellow is different from the outer diameter of the remaining bellows in the drug container 16.

Figure 2:
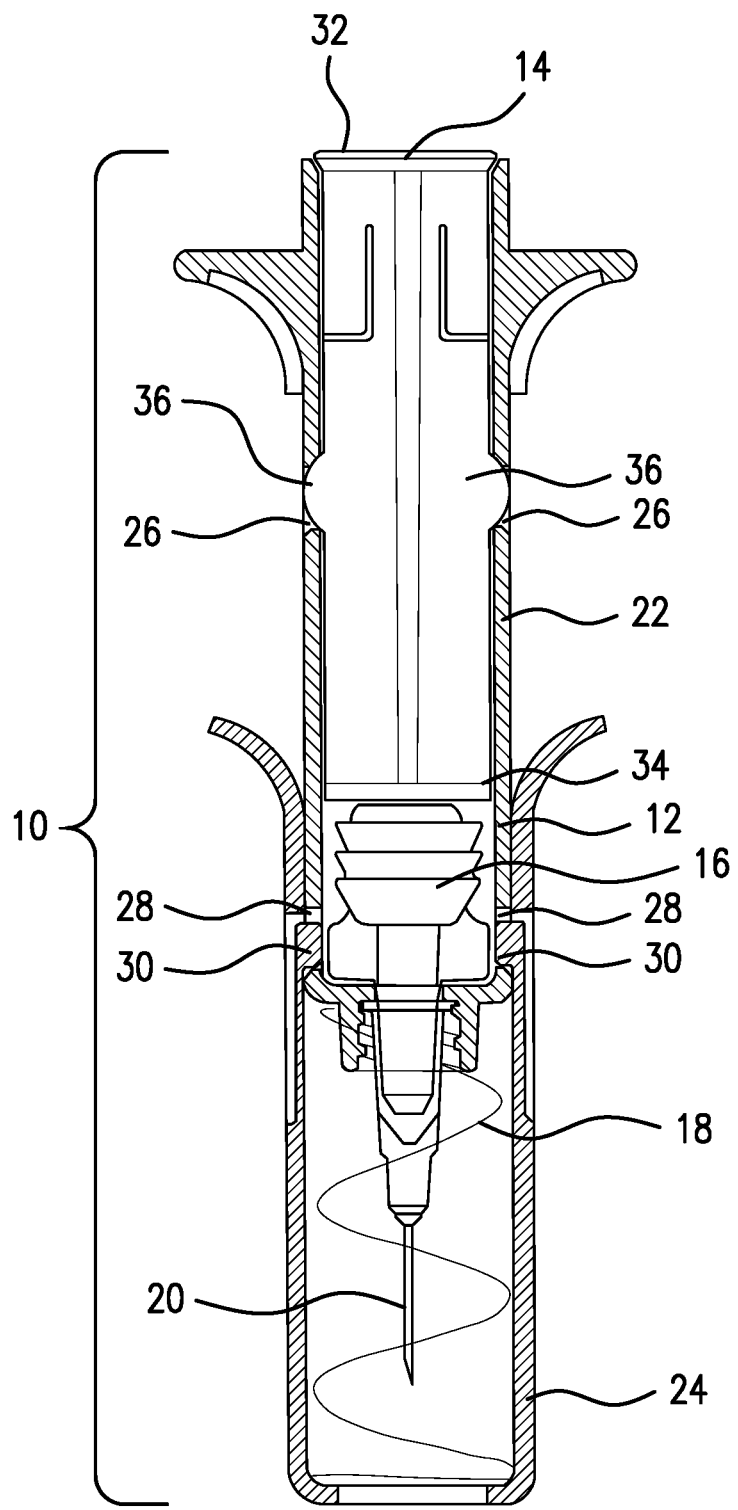
FIG. 2 is an embodiment of the drug delivery device described herein, in its post-injection position or second position wherein the safety shield is in an extended state.

FIG. 2 shows an embodiment of the drug delivery device described herein, in its post-injection position or second position wherein the safety shield is in an extended state. FIG. 2 shows a drug delivery device 10 that comprises a main body 12, a plunger 14, a drug container 16, a spring 18 and a needle 20. The main body 12 includes an inner body 22 and an outer body 24. As shown in FIG. 2, the inner body 22 has a first set of locking windows 26 and a second set of locking windows 28. The outer body 24 contains two release and lock beams 30. The outer body 24 is attached to the inner body 22 by the release and lock beams being in communication with the first set locking windows 26 or second set of locking windows 28. Specifically, as shown in FIG. 2, the outer body 24 is secured in the extended position as the lock and release beams 30 are in communication with the second set of locking windows 28.

Also, as shown in FIG. 2, the plunger 14 extends from a proximal end 32 to a distal end 34 and has release cams 36. As pressure was applied to the plunger 14 at the proximal end 32, the plunger 14 moved axially toward the drug container 16, causing the drug container 16 to compress. As the release cams 36 on the plunger 14 moved axially, the release cams 36 caused the release and lock beams 30 to disengage from the first set of locking windows 26 and cams 36 occupy the space previously occupied by the lock and release beams 30.

Once the release and lock beams 30 disengaged from the first set of locking windows 26, the spring 18 urges the outer body 24 to extend axially to shield the needle 20.

Figure 3:
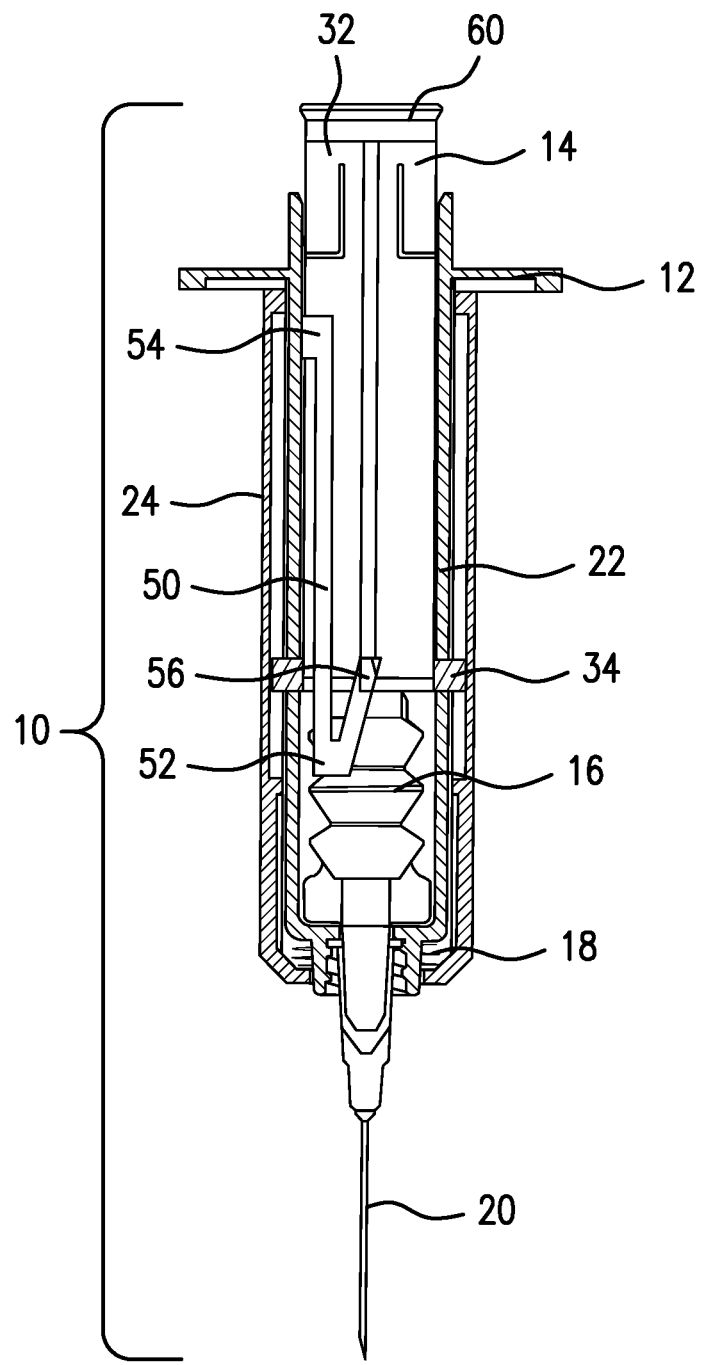
FIG. 3 is another embodiment of the drug delivery device described herein, in its pre-injection position or first position wherein the safety shield is in a retracted state.
Figure 4:
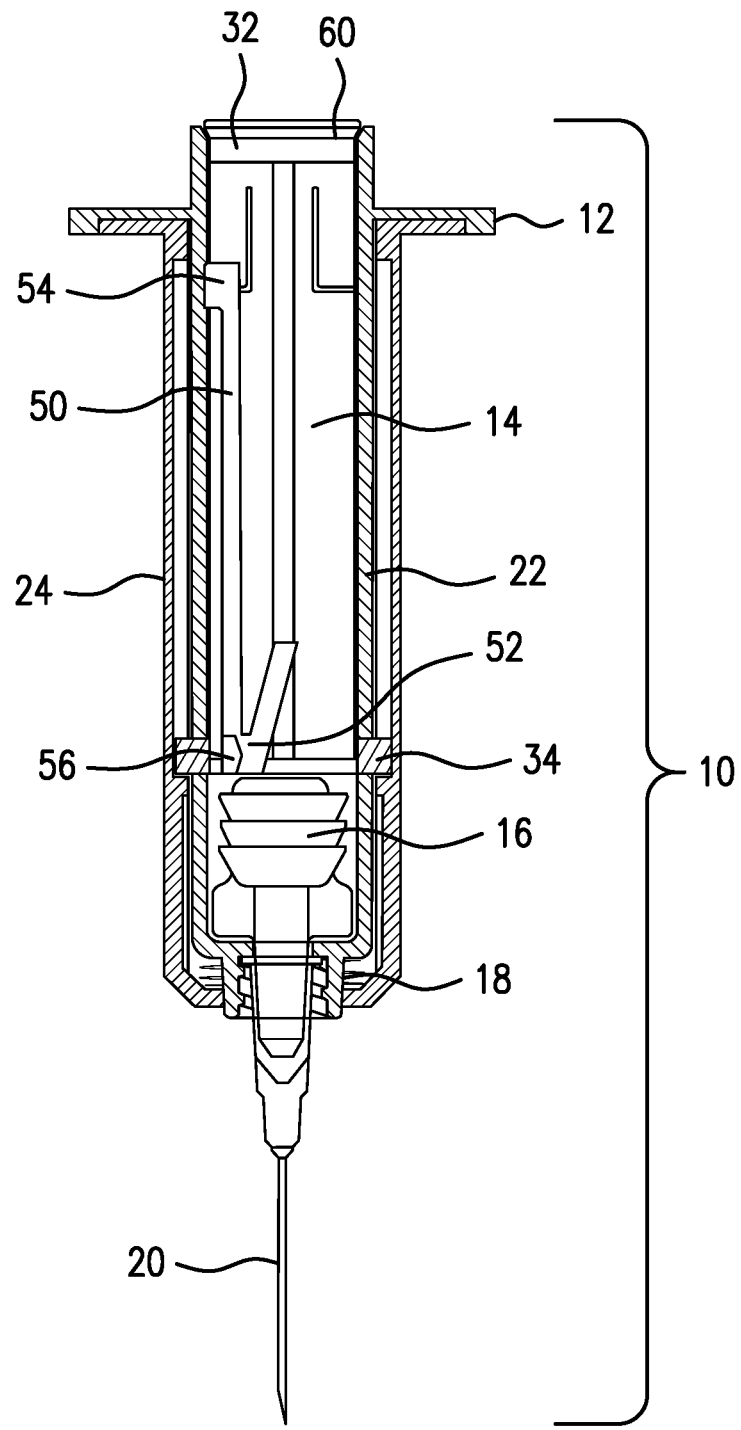
FIG. 4 is another embodiment of the drug delivery device described herein, in its pre-injection position or first position wherein the safety shield is in a retracted state.

FIG. 3 and FIG. 4 show another embodiment of the drug delivery device described herein, in its pre-injection position or first position wherein the safety shield is in a retracted state. FIG. 3 shows a drug delivery device 10 that comprises a main body 12, a plunger 14, a drug container 16, a spring 18 and a needle 20. The main body 12 includes an inner body 22 and an outer body 24. As shown in FIG. 3, the outer body 24 includes a cam track 50. The cam track has a bottom slide position 52 and a top slide position 54.

As shown in FIG. 3, the plunger 14 extends from a proximal end 32 to a distal end 34 and has a cam follower 56. As pressure is applied to the plunger at the proximal end 32. The plunger 14 moves axially toward the drug container 16, causing the drug container 16 to compress. Simultaneously, the plunger 14 and the outer body 24 will rotate as to allow the cam follower 56 to travel along the cam track 50. Plunger 14, in the embodiment shown in FIG. 3 and FIG. 4, has a freely-rotating top 60. The freely rotating top 60, allows the outer body 24 and the plunger 14 to rotate as the axial pressure is applied to the plunger 14. As shown in FIG. 4, once the drug container 16 is fully compressed, the cam follower 56 will slide into the bottom slide position 52.

Once the cam follower 56 slides into the bottom slide position 52, the spring 18 urges the outer body 24 to extend axially to shield the needle 20. This extended position is shown in FIG. 5.

Figure 5:
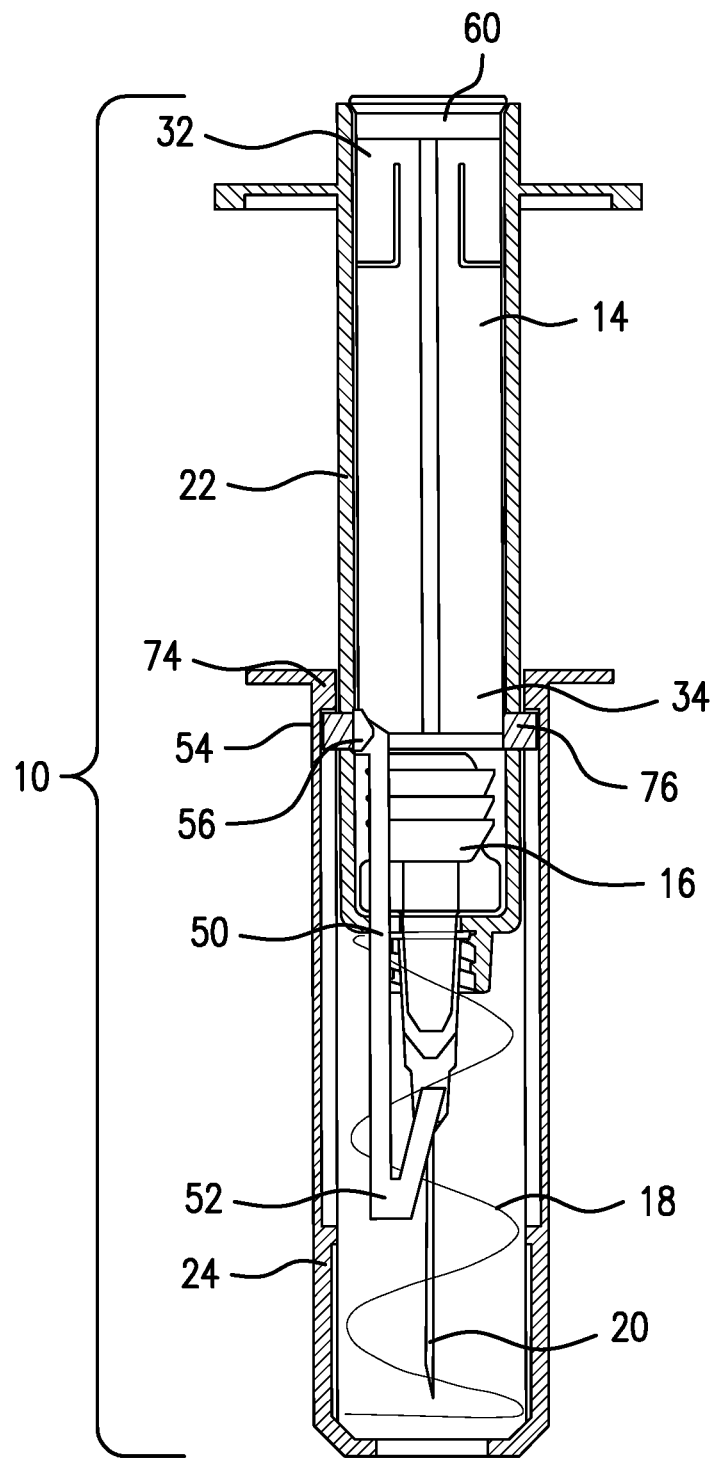
FIG. 5 is an embodiment of the drug delivery device described herein, in its post-injection position or second position wherein the safety shield is in an extended state.

FIG. 5 shows an embodiment of the drug delivery device described herein, in its post-injection position or second position wherein the safety shield is in an extended state. FIG. 5 shows a drug delivery device 10 that comprises a main body, a plunger 14, a drug container 16, a spring 18 and a needle 20. The main body includes an inner body 22 and an outer body 24. The plunger 14 extends between a proximal end 32 and a distal end 34. As shown in FIG. 5, the outer body 24 includes a cam track 50. The cam track 50 has a bottom slide position 52 and a top slide position 54.

Once the cam follower 56 slides into the bottom slide position 52, the spring 18 urges the outer body 24 to extend axially to shield the needle 20, and the cam follower 56 slides along the cam track 50 to top slide position 56, as shown in FIG. 5.

Also as shown in FIG. 5, the outer body 24 is fully extended in the extended position when outer body tabs 74 located on the proximal end of the outer body 24 meet with plunger tabs 76 located at the distal end 34 of the plunger 14.

Figure 6:
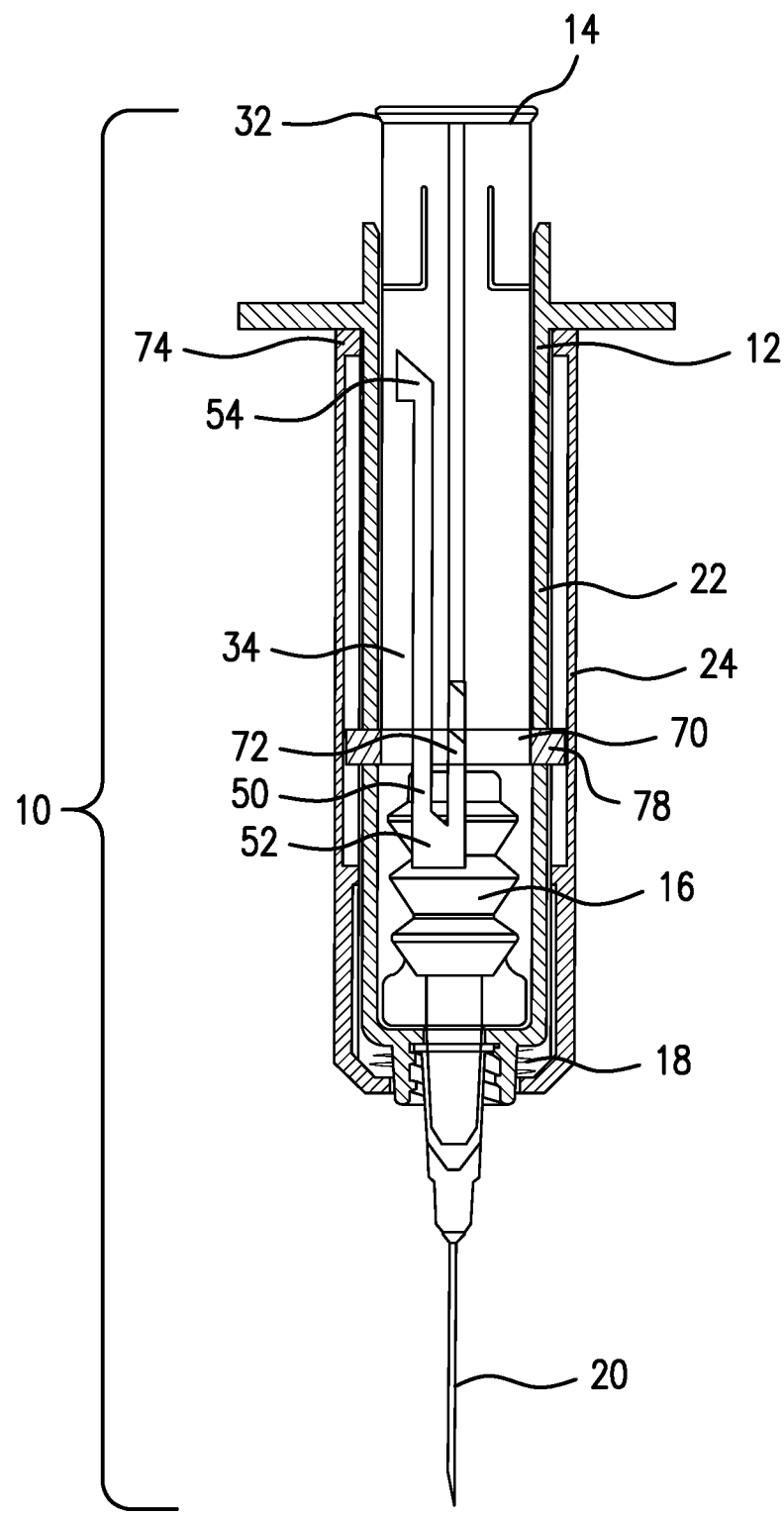
FIG. 6 is yet another embodiment of the drug delivery device described herein, in its pre-injection position or first position wherein the safety shield is in a retracted state.
Figure 7:
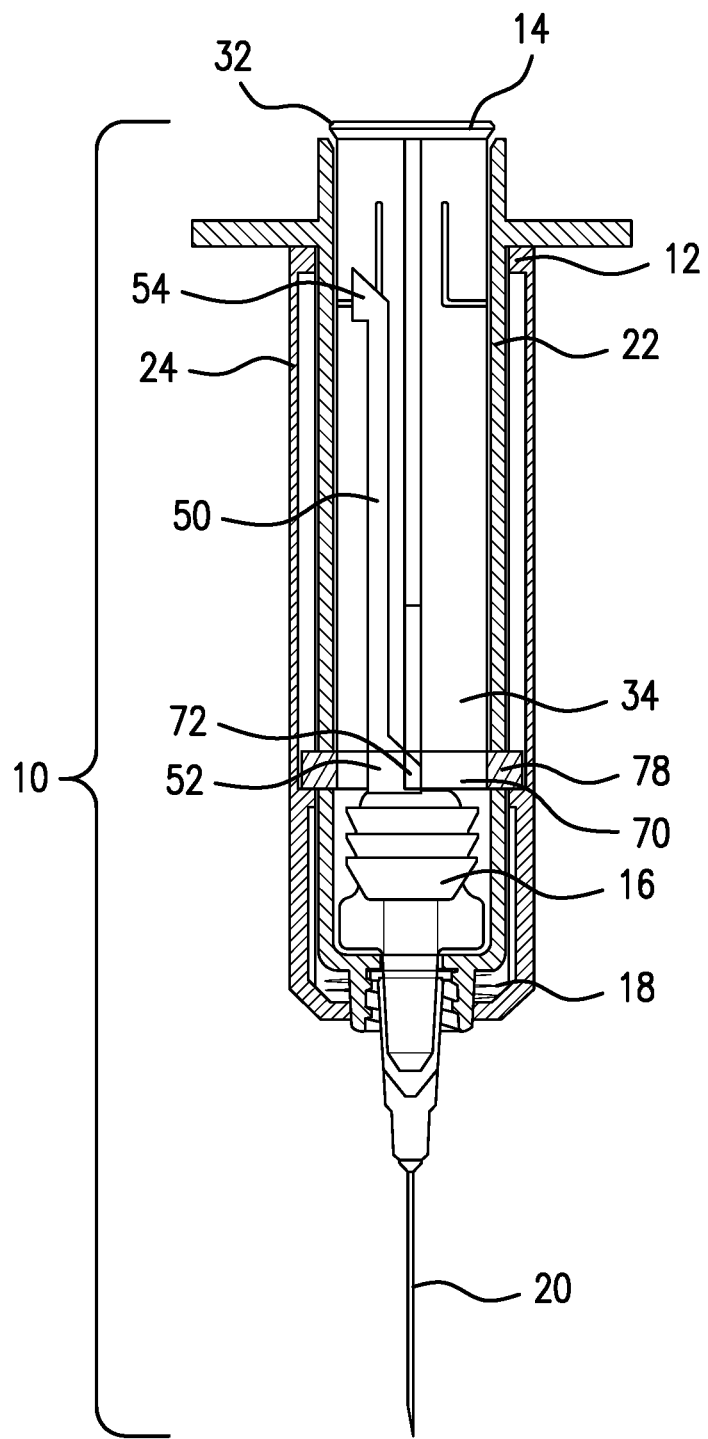
FIG. 7 is yet another embodiment of the drug delivery device described herein, in its pre-injection position or first position wherein the safety shield is in a retracted state.

FIG. 6 and FIG. 7 show yet another embodiment of the drug delivery device described herein, in its pre-injection position or first position wherein the safety shield is in a retracted state. FIG. 6 and FIG. 7 show a drug delivery device 10 that comprises a main body 12, a plunger 14, a drug container 16, a spring 18 and a needle 20. The main body 12 includes an inner body 22 and an outer body 24. As shown in FIG. 6 and FIG. 7, the outer body 24 includes a cam track 50. The cam track has a bottom slide position 52 and a top slide position 54.

As shown in FIG. 6 and FIG. 7, the plunger 14 extends from a proximal end 32 to a distal end 34. In the embodiment shown in FIG. 6 and FIG. 7, the plunger 14 has a bolt 70 with bolt tabs 78 at the distal end 34 of the plunger 14. The bolt 70 on the plunger 14 can rotate and in certain embodiments rotate freely. On the bolt 70 is a cam follower 72. As pressure is applied to the plunger at the proximal end 32. The plunger 14 moves axially toward the drug container 16, causing the drug container 16 to compress. Simultaneously, the bolt 70 and the outer body 24 will rotate as to allow the cam follower 72 to travel along the cam track 50. As shown in FIG. 7, once the drug container 16 is fully compressed, the cam follower 72 will slide into the bottom slide position 52.

Once the cam follower 72 slides into the bottom slide position 52, the spring 18 urges the outer body 24 to extend axially to shield the needle 20. This extended position is shown in FIG. 8.

Figure 8:
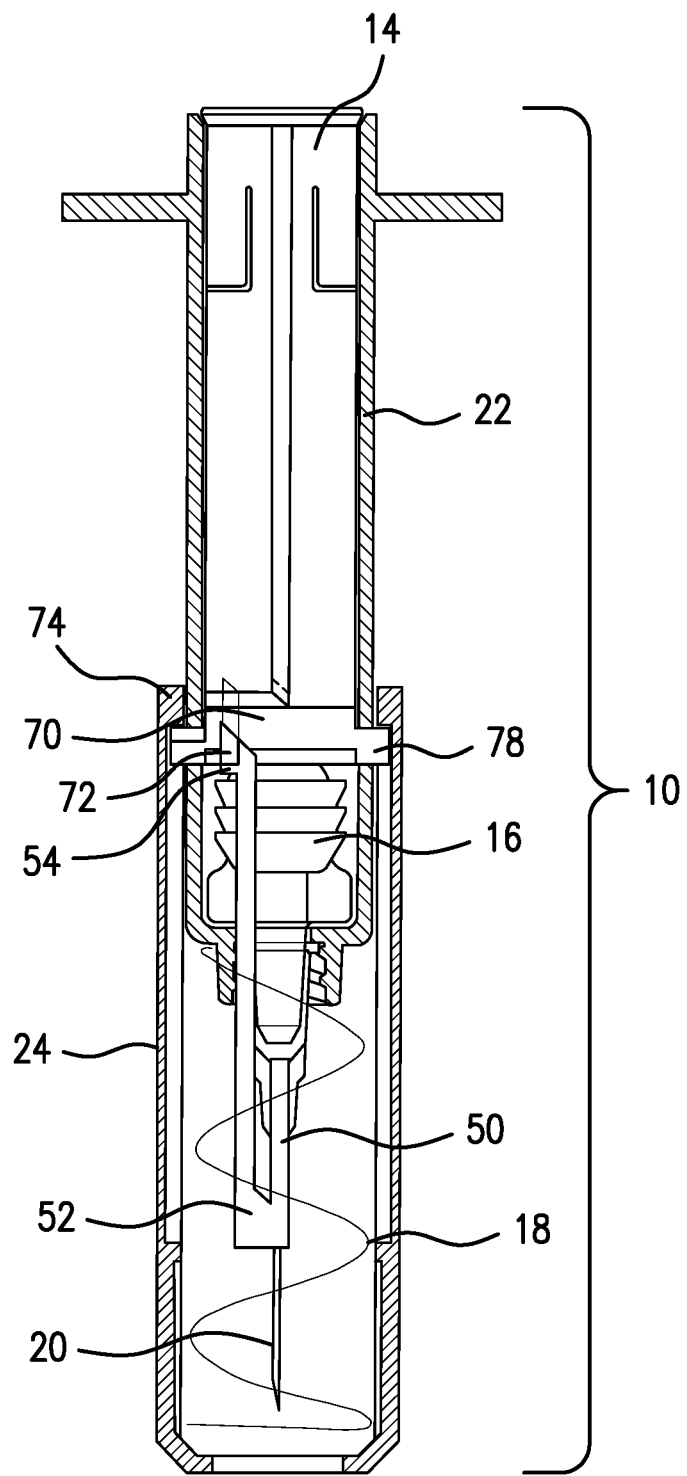
FIG. 8 is yet another embodiment of the drug delivery device described herein, in its post-injection position or second position wherein the safety shield is in an extended state.

FIG. 8 shows an embodiment of the drug delivery device described herein, in its post-injection position or second position wherein the safety shield is in an extended state. FIG. 8 shows a drug delivery device 10 that comprises a main body, a plunger 14, a drug container 16, a spring 18 and a needle 20. The main body includes an inner body 22 and an outer body 24. As shown in FIG. 8, the outer body 24 includes a cam track 50. The cam track has a bottom slide position 52 and a top slide position 54.

As shown in FIG. 8, the plunger 14 has a bolt 70 at the distal end of the plunger 14. The bolt 70 on the plunger can rotate and in certain embodiments rotate freely. On the bolt 70 is a cam follower 72. As pressure is applied to the plunger at the proximal end. The plunger 14 moves axially toward the drug container 16, causing the drug container 16 to compress. Simultaneously, the bolt 70 and the outer body 24 will rotate as to allow the cam follower 72 to travel along the cam track 50. As shown in FIG. 7, once the drug container 16 is fully compressed, the cam follower 72 will slide into the bottom slide position 52.

Once the cam follower 72 slides into the bottom slide position 52, the spring 18 urges the outer body 24 to extend axially to shield the needle 20 and the cam follower 72 slides into the top slide position 54, as shown in FIG. 8. Also as shown in FIG. 8, the outer body 24 is fully extended in the extended position when outer body tabs 74 located on the proximal end of the outer body 24 meet with bolt tabs 78 located at the distal end of the bolt 70.

Figure 9:
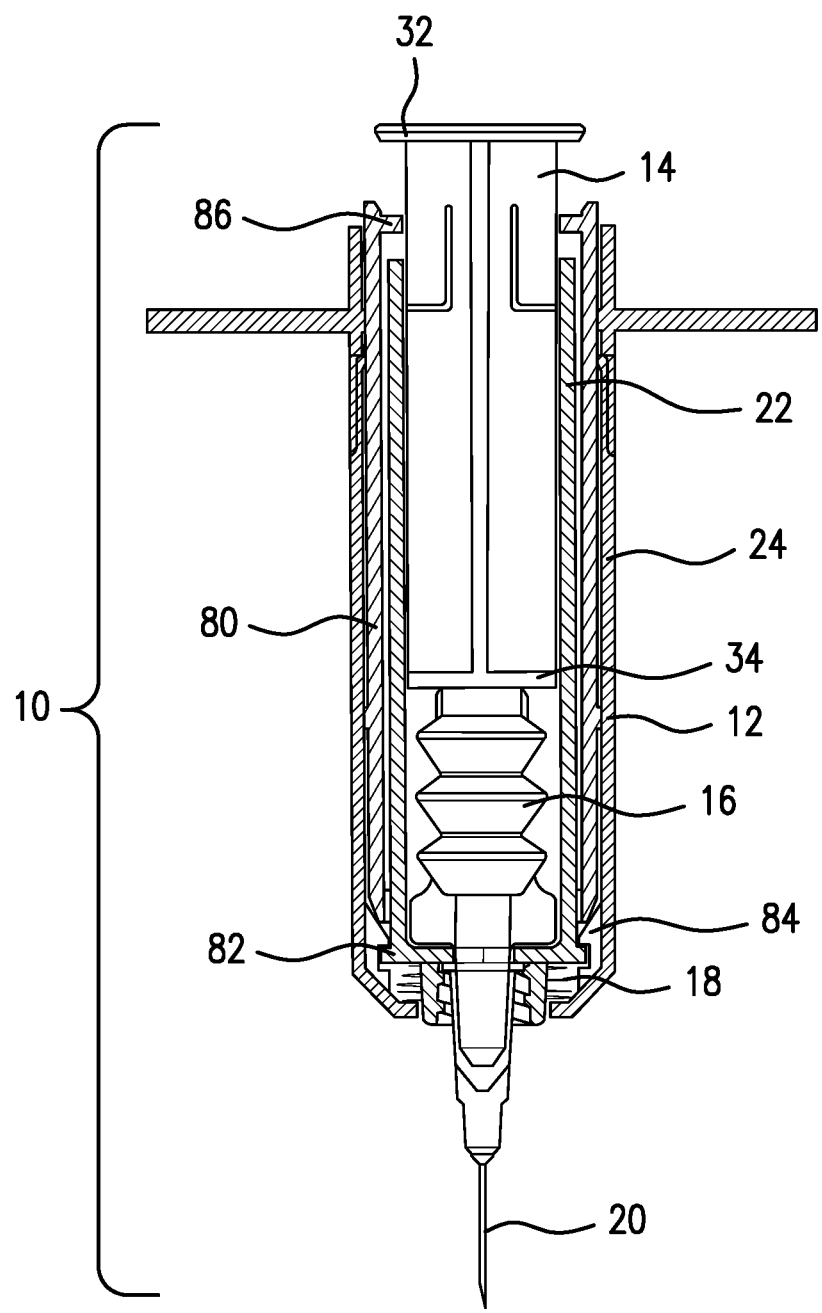
FIG. 9 is still yet embodiment of the drug delivery device described herein, in its pre-injection position or first position wherein the safety shield is in a retracted state.

FIG. 9 shows yet another embodiment of the drug delivery device described herein, in its pre-injection position or first position wherein the safety shield is in a retracted state. FIG. 9 shows a drug delivery device 10 that comprises a main body 12, a plunger 14, a drug container 16, a spring 18 and a needle 20. The main body 12 includes an inner body 22, an outer body 24 and an intermediate tube 80. As shown in FIG. 9, the intermediate tube 80 has a set of stoppers 86 at its proximal end. As shown in FIG. 9, the inner body 22 has a set of shelves 82 at the distal end of the inner body 22. The outer body 24 contains two clamps 84 having complimentary geometry to the shelves 82. The outer body 24 is attached to the inner body 22 by the clamps 84 being in communication with the shelves 82. Specifically, as shown in FIG. 9, the outer body 24 is secured in the retracted position as the clamps 84 are in communication with the shelves 82.

Also, as shown in FIG. 9, the plunger 14 extends from a proximal end 32 to a distal end 34. As pressure is applied to the plunger 14 at the proximal end 32, the plunger 14 moves axially toward the drug container 16, causing the drug container 16 to compress. The plunger also applies axial force on the stoppers 86 on the intermediate tube 80, causing the intermediate tube to move axially. The intermediate tube 80 causes the clamps 84 to disengage from the shelves 82.

Once the clamps 84 disengage from the shelves 82, the spring 18 urges the outer body 24 to extend axially to shield the needle 20. This extended position is shown in FIG. 10.

Figure 10:
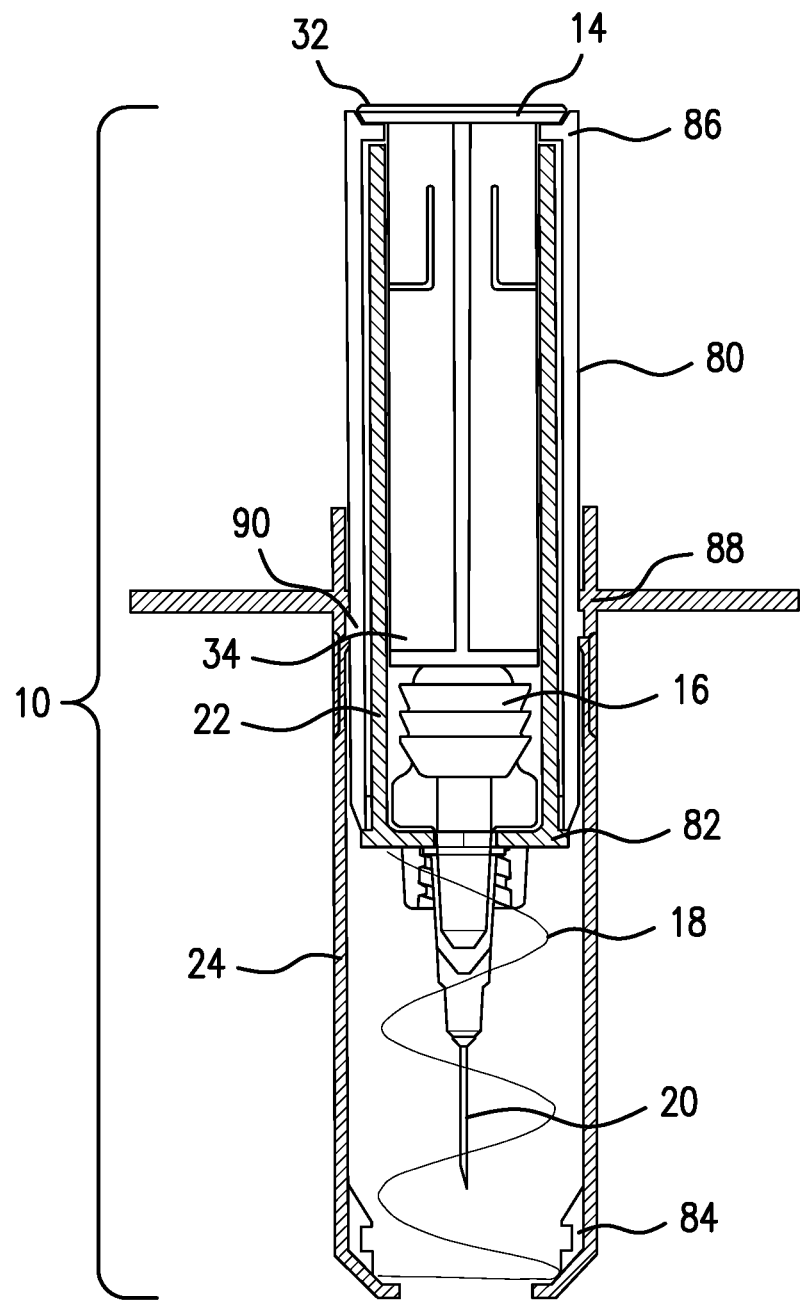
FIG. 10 is still yet another embodiment of the drug delivery device described herein, in its post-injection position or second position wherein the safety shield is in an extended state.

FIG. 10 shows an embodiment of the drug delivery device described herein, in its post-injection position or second position wherein the safety shield is in an extended state. FIG. 10 shows a drug delivery device 10 that comprises a main body, a plunger 14, a drug container 16, a spring 18 and a needle 20. The main body includes an inner body 22, an outer body 24 and an intermediate tube 80. As shown in FIG. 10, the intermediate tube 80 has a set of stoppers 86 at its proximal end. As shown in FIG. 10, the inner body 22 has a set of shelves 82 at the distal end of the inner body 22. The outer body 24 contains two clamps 84 having complimentary geometry to the shelves 82.

Also, as shown in FIG. 10, the plunger 14 extends from a proximal end 32 to a distal end 34. As pressure is applied to the plunger 14 at the proximal end 32, the plunger 14 moves axially toward the drug container 16, causing the drug container 16 to compress. The plunger 14 also applies axial force on the stoppers 86 on the intermediate tube 80, causing the intermediate tube 80 to move axially. The intermediate tube 80 causes the clamps 84 to disengage from the shelves 82.

Once the clamps 84 disengage from the shelves 82, the spring 18 urges the outer body 24 to extend axially to shield the needle 20. As shown in FIG. 10, the outer body 24 is fully extended in the extended position when outer body tabs 88 located on the proximal end of the outer body 24 meet with intermediate tube tabs 90 located on the intermediate tube.

Figure 11:
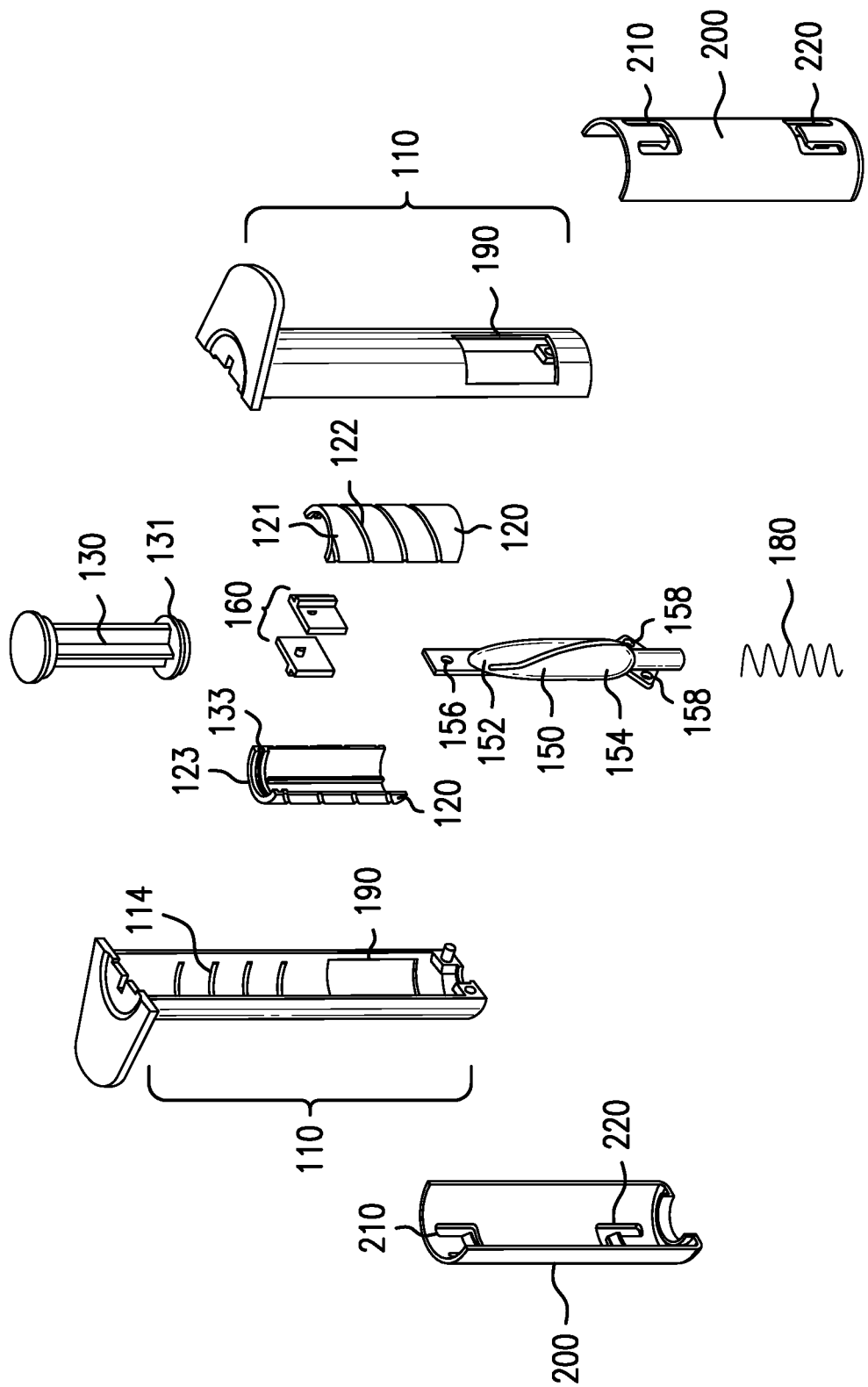
FIG. 11 is an exploded view of another embodiment of a drug delivery device described herein.

FIG. 11 is an exploded view of another embodiment of a drug delivery device described herein. FIG. 11 shows a drug delivery device that comprises a main body comprising an inner body 110 and an outer body 200. Inner body 110 has a pair of viewing windows 190. The outer body 110 has two pairs of release and lock tabs, a first set of release and lock tabs 220 and a second set of release and lock tabs 210. The inner body 110 houses a plunger 130, a screw 120 with raised helical threads 122, and a drug container 150. As shown in FIG. 11, the drug delivery device includes a spring 180, which when the drug delivery device is assembled the spring is housed between the inner body 110 and the outer body 200.

Figure 12:
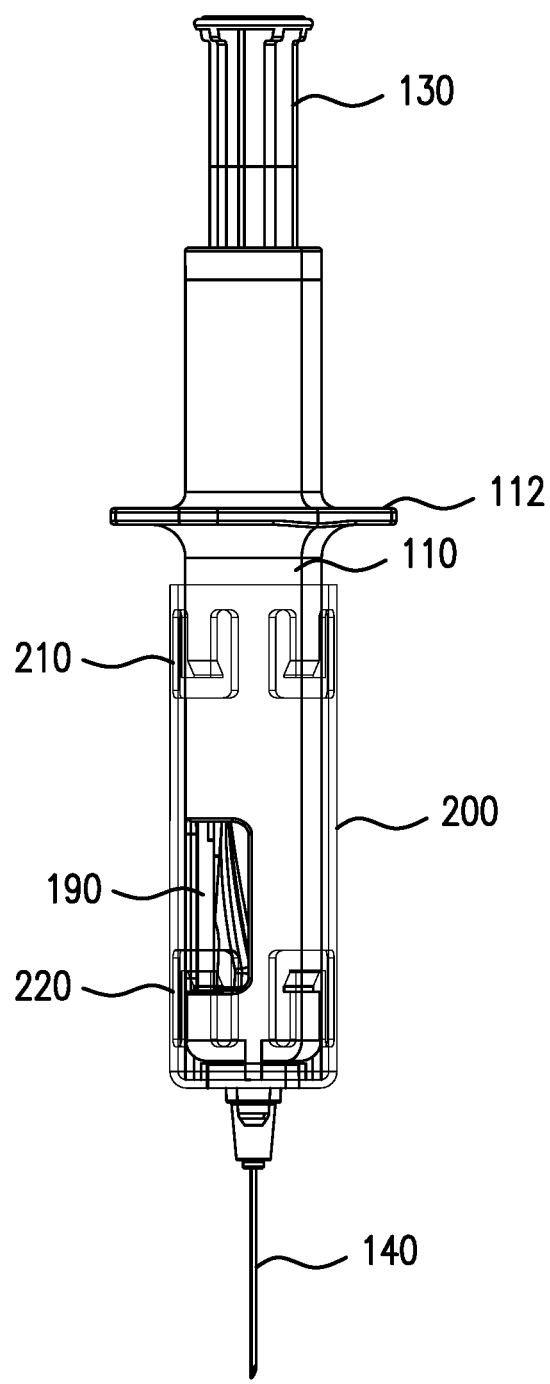
FIG. 12 is yet another embodiment of the drug delivery device described herein, in its pre-injection position or first position wherein the safety shield is in a retracted state.
Figure 13:
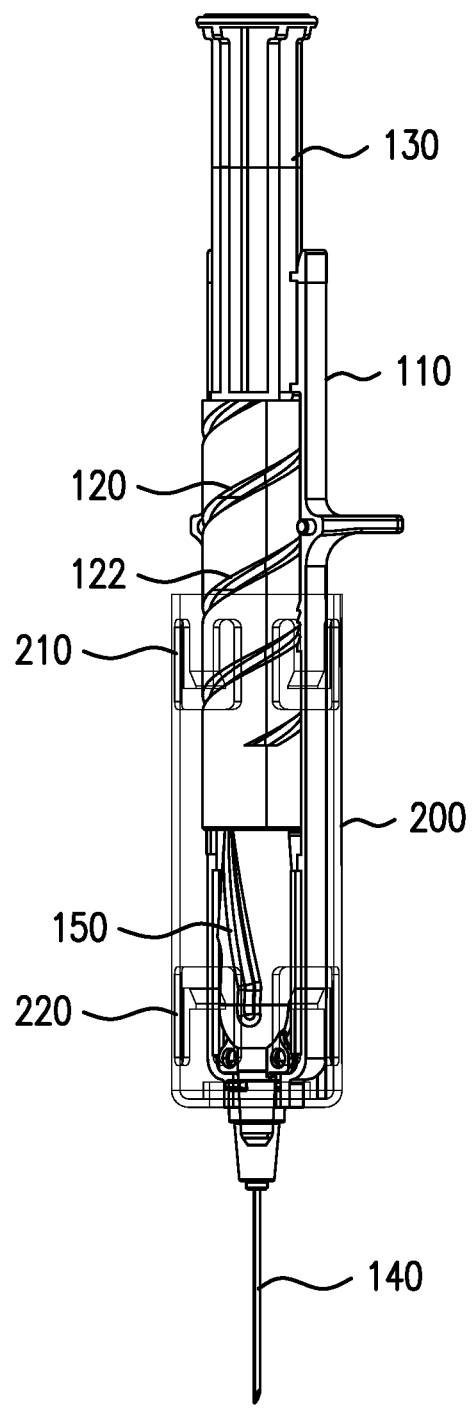
FIG. 13 is a cut away view of yet another embodiment of the drug delivery device described herein, in its pre-injection position or first position wherein the safety shield is in a retracted state.

When the drug delivery device of FIG. 11 is assembled, the outer body 200 is connected to the inner body 110 in a first or pre-injection position by attachment of the first pair of release and lock tabs 220 to the viewing windows 190. The assembled drug delivery device of FIG. 11 in the first or pre-injection position is shown in FIGS. 12 and 13.

The drug delivery device of FIG. 11 also includes a screw 120. In the embodiment shown in FIG. 11, the screw 120 is a hollow cylinder comprising two halves, a first half 121 and a second half 123, wherein each half comprises an outer surface with external raised helical threads 122. The helical threads 122 can mate with internal helical threads 114 in located inside the inner body 110. As shown in FIG. 11, the external raised helical threads 122 span the entire length of the screw 120. In other embodiments, the external raised helical 122 threads can span less than the entire length of the screw 120.

The drug delivery device of FIG. 11 also includes a plunger 130. As shown in FIG. 11, the distal end of the plunger 130 engages the screw 120 at the proximal end of the screw 120. In FIG. 11, the plunger 130 has a circumferential projection 131 that engages a circumferential groove 133 on the screw. The engagement prevents relative motion in an axial direction between the plunger 130 and the screw 120, but permits rotational motion between the plunger 130 and the screw 120. Application of axial force in the distal direction to the proximal end of the plunger 130 causes axial movement of the plunger 130 in the distal direction of the plunger 130. This motion is transferred to the screw 120 by the engagement between the plunger 130 and the screw 120. The threaded engagement between the external threads 122 of the screw 120 and the internal threads 114 of the inner body 110 causes the screw 120 to rotate as it moves in an axial direction within the inner body 110.

Figure 14:
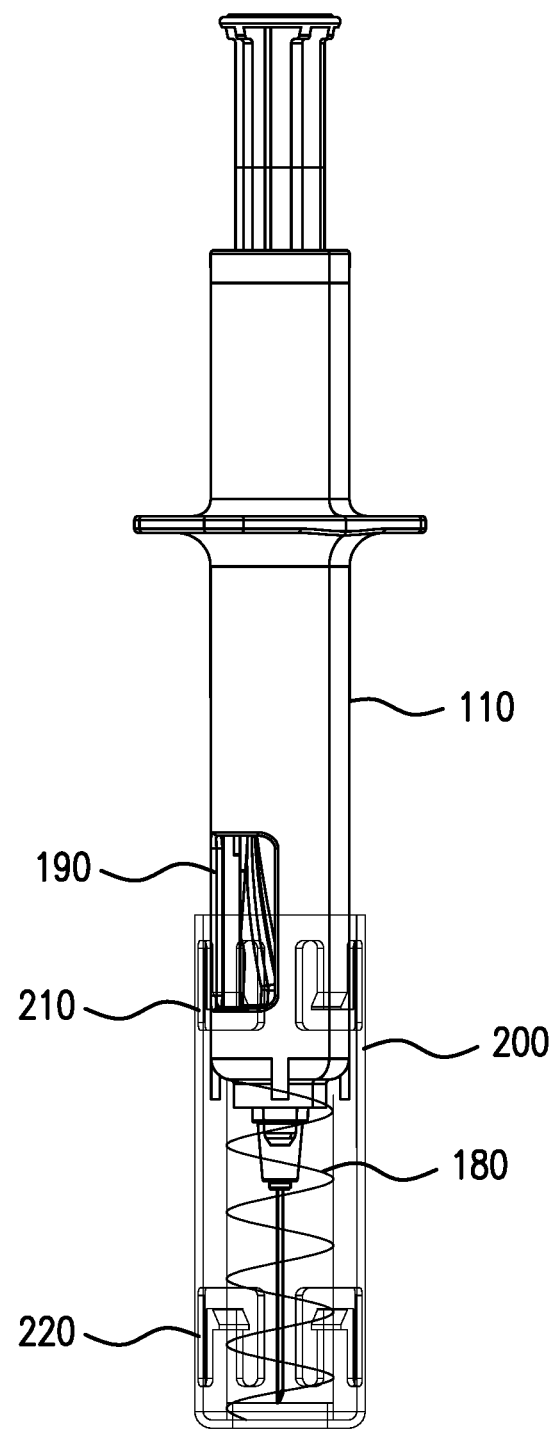
FIG. 14 is yet another embodiment of the drug delivery device described herein, in its post-injection position wherein the safety shield is in an extended state.
Figure 15:
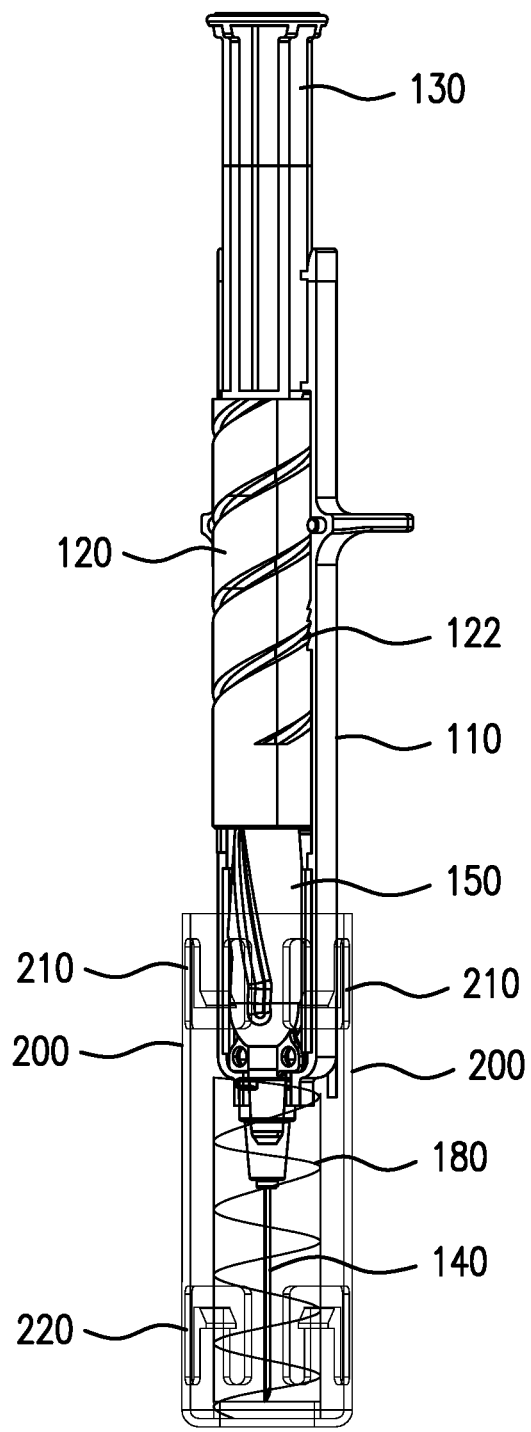
FIG. 15 is a cut away view of yet another embodiment of the drug delivery device described herein, in its post-injection position wherein the safety shield is in an extended state.

As the screw rotates and moves through the viewing windows 190, the raised helical threads 122 of the screw 120 disengage the first pair of release and lock tabs 220 from the viewing windows 190 of the inner body 110. The spring 180 can then urge the outer body 200 to extend axially to shield a needle (not shown). This extended position is shown in FIGS. 14 and 15.

The device shown in FIG. 11 also comprises a drug container 150. The drug container 150 tapers from its distal end 154 to its proximal end 152. The drug delivery device also includes a clamp 160 that secures the drug container 150 to the screw 120. The drug container 150 comprises a securing mechanism at its proximal end 152, wherein the drug container 150 is secured to the clamp 160 at the proximal end 152 of the drug container 150.

In FIG. 11 the securing mechanism is a hole 156 at the proximal end 152 of the drug container 150. In this embodiment the drug container 150 also has a securing mechanism at its distal end 154, wherein the drug container 150 is secured to the inner body 110 at the distal end 154 of the drug container 150. The securing mechanism is a set of two holes 158 located at the distal end 154.

FIGS. 12 and 13 show the first position or pre-injection position of an assembled drug delivery device of FIG. 11. FIG. 12 shows a drug delivery device comprising a main body which includes as inner body 110 and an outer body 200. Inner body 110 has viewing windows 190. The outer body 200 has two pairs of release and lock tabs, a first set of release and lock tabs 220 and a second set of release and lock tabs 210. The outer body 200 is connected to the inner body 110 in a first position or pre-injection position by attachment of the first set of release and lock tabs 220 to the viewing windows 190. In FIG. 12, inner body 110 has finger flanges 112 and houses a plunger 130. Also in FIG. 12, a needle 140 is attached to inner body 110.

FIG. 13 is a partial cutaway view of the assembled drug delivery device of FIG. 11 in its first position or pre-injection position. As shown in FIG. 13, the device has an inner body 110. The inner body includes viewing windows (not shown) to view the drug container 150. The drug delivery device shown in FIG. 13 has an outer body 200. The outer body 200 has two pairs of release and lock tabs, a first set of release and lock tabs 220 and a second set of release and lock tabs 210. The outer body 200 is connected to the inner body 110 in a first position or pre-injection position by attachment of the first set of release and lock tabs 220 to the viewing windows (not shown).

As shown in FIG. 13, the drug delivery device includes a screw 120. The screw 120 is a hollow cylinder with external raised helical threads 122. As shown in FIG. 13, the raised helical threads 122 span the entire length of the screw 120. In other embodiments, the external mating threads can span a portion or less than the entire length of the screw.

The drug delivery device of FIG. 13 also includes a plunger 130. As shown in FIG. 13, the distal end of the plunger 130 engages the screw 120 at the proximal end of the screw 120. The engagement prevents relative motion in an axial direction between the plunger 130 and the screw 120. The engagement permits rotational relative motion between the plunger 130 and the screw 120, whereby application of an axial force in the distal direction to the plunger 130 causes axial movement in a distal direction of the screw 120 and rotation of the screw 120. As the screw 120 rotates and moves through the viewing windows (not shown), the raised helical threads 122 of the screw 120 disengage the first set of release and lock tabs 220 from the viewing windows (not shown) of the inner body 110. A spring (not shown) located between the inner body 110 and the outer body urges the outer body 200 to extend axially to shield the needle 140. This extended position is shown in FIGS. 14 and 15. Additionally, the combined movement and rotation of the screw 120 causes the drug container 150 to twist, thereby emptying its contents.

FIGS. 14 and 15 show the post-injection position or second position of an assembled drug delivery device of FIG. 11. FIG. 14 shows a drug delivery device comprising a main body which includes an inner body 110 and an outer body 200. The inner body has viewing windows 190. The outer body 200 has two pairs of release and lock tabs, a first set of release and lock tabs 220 and a second set of release and lock tabs 210. The outer body 200 is connected to the inner body 110 in a post-injection position by attachment of the second set of release and lock tabs 210 to the viewing windows 190. Also shown in FIGS. 14 and 15 is a spring 180 which is capable of urging outer body 200 slidable over inner body 110.

FIG. 15 is a partial cutaway view of the assembled drug delivery device of FIG. 11 in its post-injection position. As shown in FIG. 15, the device has an inner body 110. The inner body includes viewing windows (not shown) to view the drug container 150. The drug delivery device shown in FIG. 15 has an outer body 200. The outer body 200 has two pairs of release and lock tabs, a first set of release and lock tabs 220 and a second set of release and lock tabs 210. The outer body is connected to the inner body 110 in a post-injection position by attachment of the second set of release and lock tabs 210 to the viewing windows (not shown).

As shown in FIG. 15, the drug delivery device includes a screw 120. The drug delivery device of FIG. 15 also includes a plunger 130. As shown in FIG. 15, the distal end of the plunger 130 engages the screw 120 at the proximal end of the screw 120. The engagement prevents relative motion in an axial direction between the plunger 130 and the screw 120. The engagement permits rotational relative motion between the plunger 130 and the screw 120, whereby application of an axial force in the distal direction to the plunger 130 causes axial movement in a distal direction of the screw 120 and rotation of the screw 120. As the screw 120 rotates and moves through the viewing windows (not shown), the raised helical threads 122 of the screw 120 disengage the first set of release and lock tabs 220 from the viewing windows (not shown) of the inner body. A spring 180 located between the inner body and the outer body urges the outer body to extend axially to shield the needle 140. The axial movement of the outer body 200 is stopped by the second set of release and lock tabs 210 on the outer body 200 connecting and attaching to the viewing windows (not shown) of the inner body 110.

The drug delivery device can be used to deliver any type of drug product that can be delivered via a syringe. In certain embodiments of the drug delivery device described herein, the drug product in the drug container may comprise one or more of the following: human papillomavirus quadrivalent vaccine, recombinant; human papillomavirus 9-valent vaccine, recombinant; *Haemophilus* B conjugate vaccine or meningococcal protein conjugate; hepatitis B vaccine, recombinant; *Haemophilus* B conjugate; hepatitis B (recombinant) vaccine; hepatitis A vaccine, inactivated; pneumococcal vaccine polyvalent; artemether; cyclimorph (morphine and cyclizine); cyclizine; morphine; codeine; chlorphenamine; fosphenytoin sodium; chlorpromazine; haloperidol; epinephrine; hydroxocobalamin; heparin sodium; phytomenadione; atropine; furosemide; lidocaine; dalteparin sodium; digoxin; amiodarone; dextran 70; glucagon-like peptide; polygeline; hyoscine hydrobromide; oxytocin and ergometrine; oxytocin; carbetocin; magnesium sulfate; dexamethasone; metooclopramide; ondansetron; ketamine; neostigmine; pyridostigmine; dimercaprol; ranitidine; testosterone; calcium gluconate; diazepam; acetylcysteine; sulfamethoxazole+trimethoprim; hydroxocobalamin; protamine sulfate; tranexamic acid; verapamil; anti-D immunoglobulin (human); diphtheria antitoxin; suxamethonium; fluphenazine; salbutamol; pediatric hexavalent combination vaccine for *Haemophilus* influenzae type B conjugate, recombinant hepatitis B surface antigen, diphtheria, tetanus, 5-component acellular pertussis, and inactivated poliovirus Types 1, 2, and 3; BCG Vaccine; cholera vaccine; dengue vaccine; diphtheria vaccine; ebola vaccine; *Haemophilus* influenzae type B vaccine; herpes simplex virus vaccine; influenza vaccine; Japanese encephalitis vaccine; measles vaccine; meningococcal meningitis vaccine; mumps vaccine; norovirus vaccine; pertussis vaccine; pneumococcal vaccine; poliomyelitis vaccine; rabies vaccine; respiratory syncytial virus vaccine; rotavirus vaccine; rubella vaccine; tetanus vaccine; typhoid vaccine; varicella vaccine; yellow fever vaccine. In certain embodiments of the drug delivery device described herein, the drug container is pre-filled with a drug such as oxytocin or carbetocin.

Also described herein are methods of manufacturing the drug delivery devices described herein. The drug container may be produced using a variety of manufacturing methods. In certain embodiments, the drug container is manufactured by blow-fill-seal technology (BFS). In other embodiments, the drug container is manufactured by form-fill-seal technology (FFS).

In preferred embodiments, the drug container is made of thin flexible plastic. The drug container and housing of the delivery devices described herein are preferably made of a biocompatible, non-biodegradable polymer. Suitable biocompatible, non-biodegradable polymers include but are not limited to, a polyacrylate; a polymer of ethylene-vinyl acetate; an acyl-substituted cellulose acetate; a non-degradable polyurethane; a polystyrene; a polyvinyl chloride; a polyvinyl fluoride; a poly(vinyl imidazole); a chlorosulphonate polyolefin; a polyethylene oxide; a polyethylene; a polypropylene; a metallocene plastomer, a thermoplastic elastomer, an acrylic, a polycarbonate, an acrylonitrile-butadiene-styrene, a multi-layer barrier film; or a blend, combination, or copolymer thereof. Each component of the drug delivery device described herein can be made of the same or different biocompatible, non-biodegradable polymer. In certain embodiments, a multi-layer barrier film may be used, depending on drug container performance requirements. It should be obvious to those skilled in the art that most of these alternate embodiments may be combined to create a drug container with desired attributes suitable for specific applications.

The embodiments illustrated and discussed in this specification are intended only to teach those skilled in the art the best way known to the inventors to make and use the invention. Nothing in this specification should be considered as limiting the scope of the present invention. All drawings presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

What is claimed is:

1. A drug delivery device comprising:
   a drug container comprising at least one bellow, wherein each and every bellow of the at least one bellow comprises a first surface and an opposing second surface, wherein the first surface is comprised of a first Belleville spring and the opposing second surface is comprised of a second Belleville spring, wherein the second Belleville spring has a higher spring rate than the first Belleville spring, wherein the drug container has a first, expanded position and a second, stable position, wherein due to the relative spring rates of the first and second Belleville springs, when an axial load is applied to the drug container in the expanded position, the second Belleville spring remains static, as the first Belleville spring deflects, such that the first Belleville spring inverts and nests inside of the second Belleville spring and due to the first Belleville spring being inverted and nesting inside of the second Belleville spring, there is no restoring force which prevents the drug container from returning to the expanded position, wherein when the drug container is in the second, stable position the drug container cannot be refilled or reused;
   a needle, wherein while the drug container is the first expanded position and in the second, stable position the needle is in continuous liquid communication with the drug container;
   a plunger wherein the plunger extends between a proximal end and a distal end and wherein the plunger is in communication with the drug container where upon axial movement of the plunger, the drug container is compressed;
   a main body extending between a proximal end and a distal end and comprising an inner body and an outer body, wherein the inner body houses the plunger and the drug container and the outer body is capable of sliding over the inner body and extending past the needle, wherein the outer body further comprises a set of release and lock beams, and wherein the inner body further comprises a set of locking windows, wherein the set of release and lock beams is engaged with the set of locking windows when the outer body is in a retracted position; and a spring located between the inner body and the outer body for urging the outer body to slide over the inner body and extend past the needle.

2. The drug delivery device of claim 1, wherein the plunger comprises at least one release cam where upon axial movement of the plunger, the at least one release cam can cause disengagement of the set of release and lock beams of the outer body from the set of locking windows the inner body causing the outer body to move slidingly along the inner body.

3. The drug delivery device of claim 1, wherein the inner body further comprises a second set of locking windows, wherein when the set of release and lock beams is engaged with the second set of locking windows the outer body is in an extended position.

4. The drug delivery device of claim 1, wherein the drug container further comprises a drug product.

* * * * *